United States Patent [19]

Gonzalez-Cadavid et al.

[11] Patent Number: 5,594,032
[45] Date of Patent: Jan. 14, 1997

[54] AMELIORATION OF HUMAN ERECTILE DYSFUNCTION BY TREATMENT WITH INOS, INDUCERS OF INOS OR INOS CDNA

[76] Inventors: Nestor F. Gonzalez-Cadavid, 3350 Calvert Rd., Pasadena, Calif. 91107; Jacob Rajfer, 16 Quarterhorse La., Rolling Hills Estates, Calif. 90274

[21] Appl. No.: 337,357

[22] Filed: Nov. 10, 1994

[51] Int. Cl.$^6$ ................................... A61K 31/13
[52] U.S. Cl. ..................... 514/645; 514/740; 435/195; 435/212; 435/226; 435/228; 530/395
[58] Field of Search ........................ 514/645, 740; 530/395; 435/195, 212, 220, 228

[56] References Cited

U.S. PATENT DOCUMENTS

| | | | |
|---|---|---|---|
| 4,801,587 | 1/1989 | Voss et al. | 514/248 |
| 4,931,445 | 6/1990 | Goldstein et al. | 514/252 |
| 5,132,407 | 7/1992 | Stuehr et al. | 530/395 |
| 5,256,652 | 10/1993 | El-Rashidy | 514/58 |
| 5,268,465 | 12/1993 | Bredt et al. | 435/252.3 |
| 5,278,192 | 1/1994 | Fung et al. | 514/645 |
| 5,336,678 | 8/1994 | Cavallini | 514/275 |

FOREIGN PATENT DOCUMENTS

94/16729  8/1994  WIPO.

*Primary Examiner*—Paul J. Killos
*Attorney, Agent, or Firm*—Oblon, Spivak, McClelland, Maier & Neustadt, P.C.

[57] ABSTRACT

Treatment of erectile dysfunction comprising administering to a patient, inducible Nitric Oxide Synthase (iNOS) agents, including penile iNOS, inducers of penile iNOS, iNOS cDNA, or penile smooth muscle cells transformed with iNOS cDNA. Typical in vivo treatment involves delivery of these agents to the penile tissue of a patient by constant or intermittent implanted or external infusion pump, by implantation of time-release microcapsules or introduction of the genetically-engineered cells as by injection. Also disclosed are methods of treatment involving in vitro induction of iNOS in cultured smooth muscle cells and thereafter delivery of purified or recombinant iNOS enzyme, production of iNOS cDNA and genetic transformation with iNOS cDNA, followed by delivery thereof to the penis of a patient.

11 Claims, 15 Drawing Sheets

Fig_1

Fig_2

Fig_3

Fig_4

Fig_8

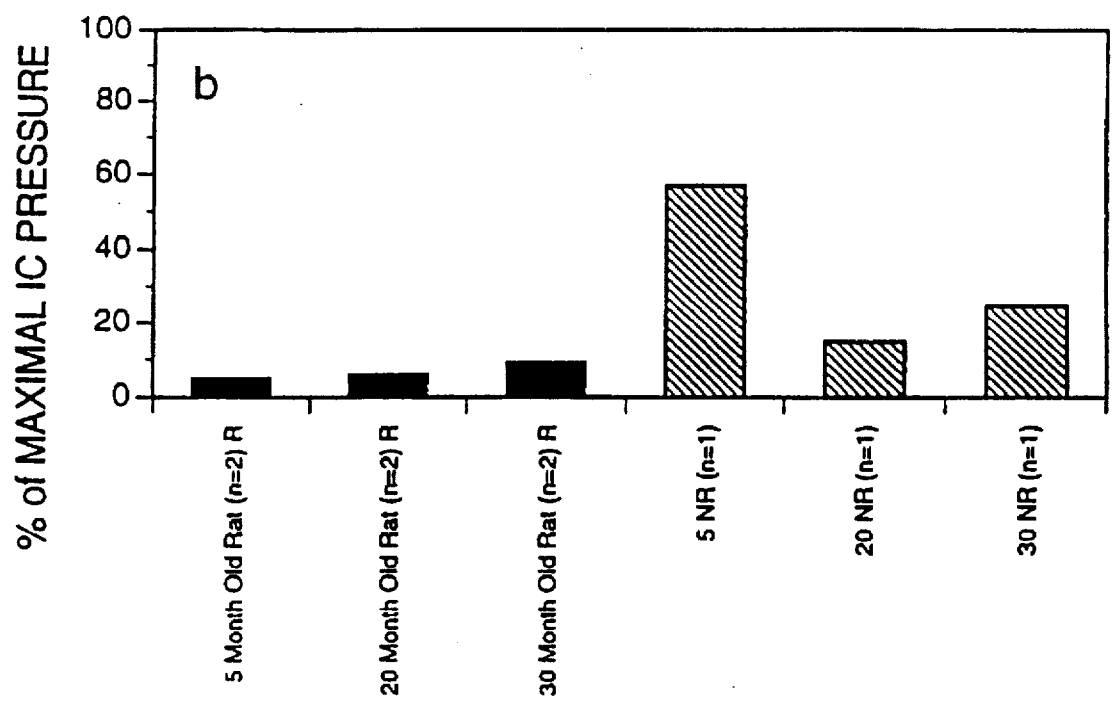
Fig_11

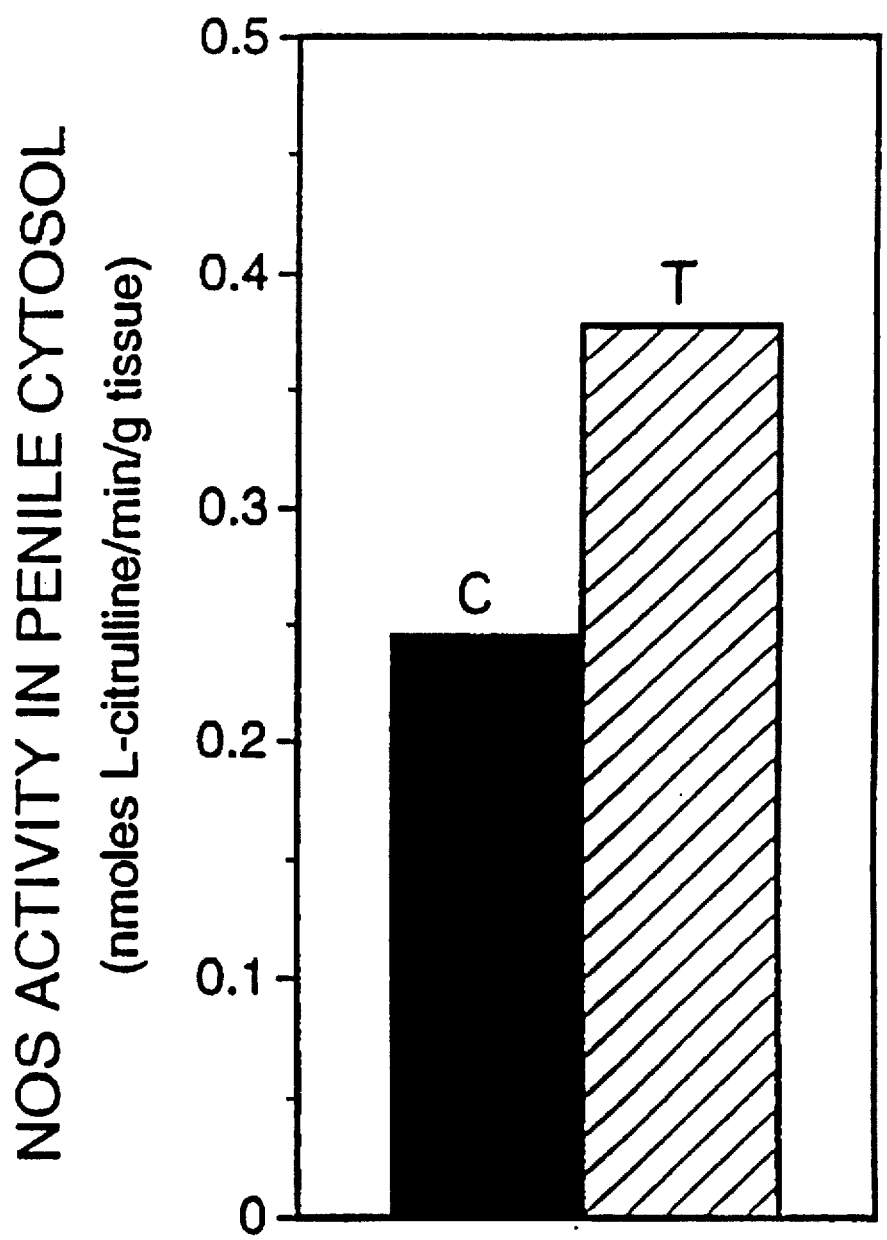
Fig_12

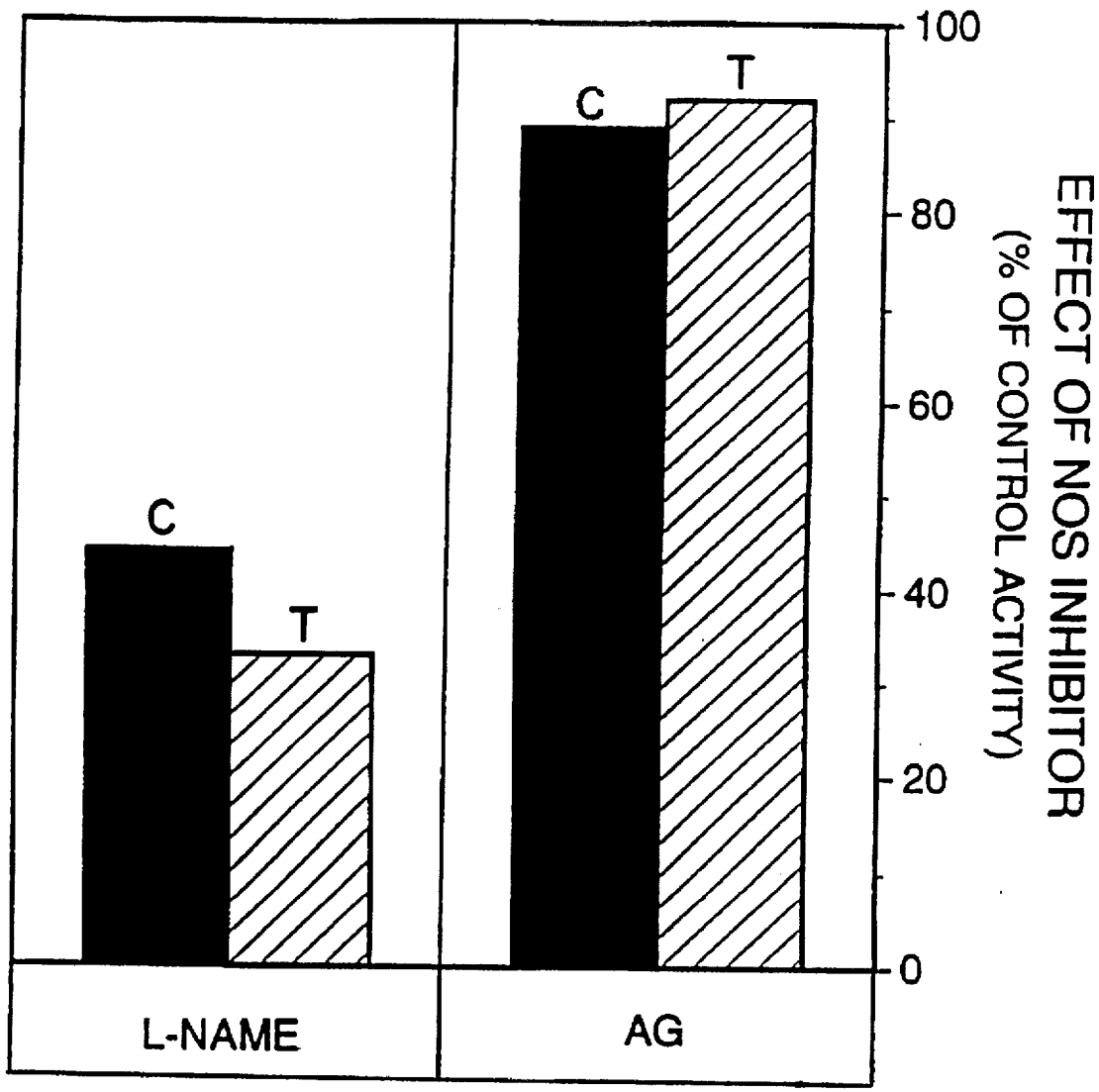
Fig_13

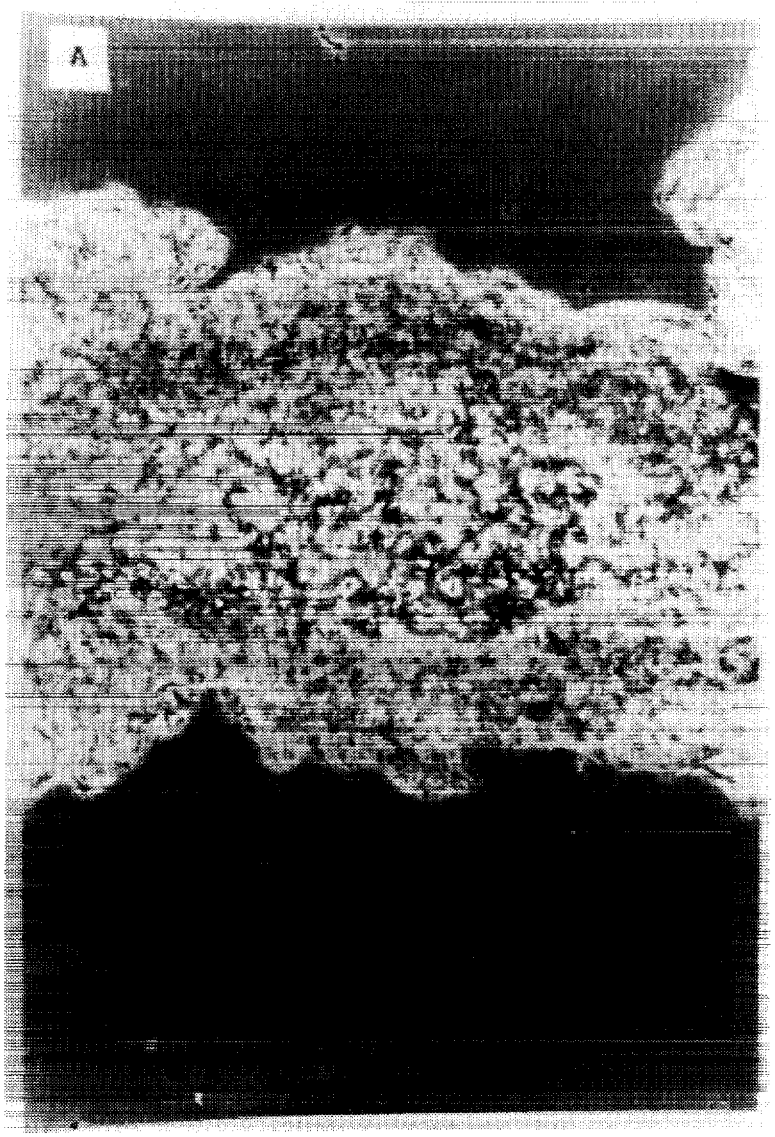
Fig_14A

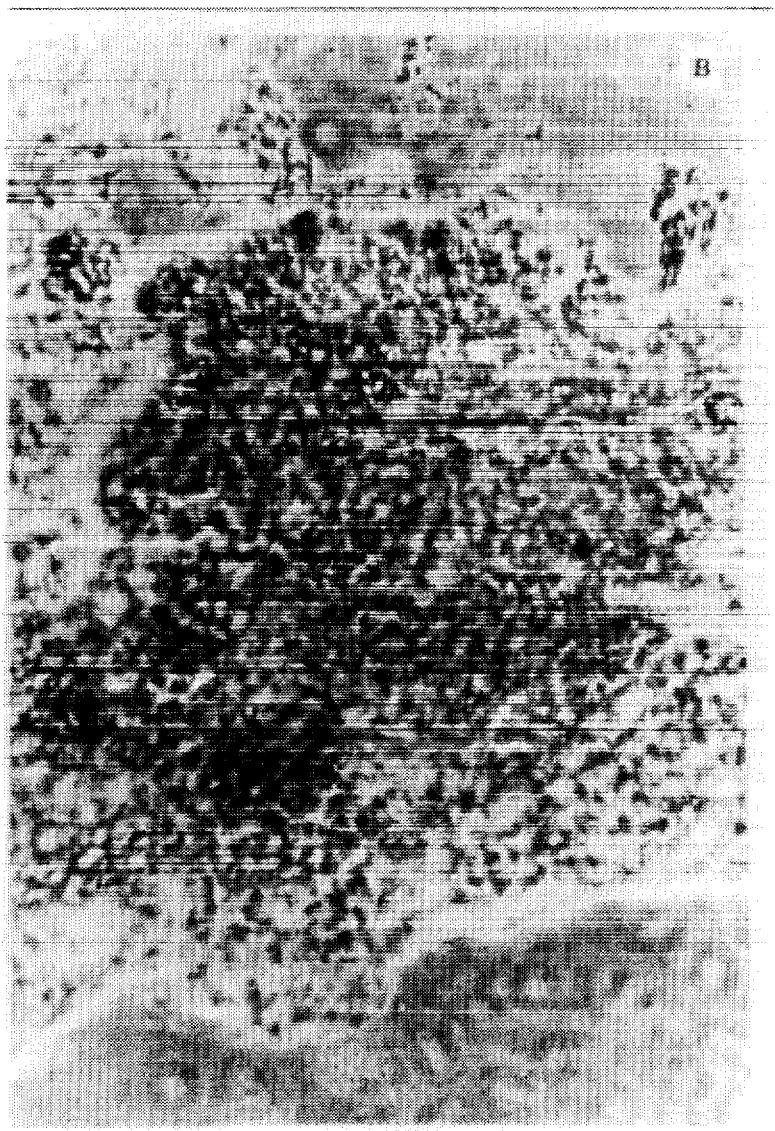
Fig._14B 5,594,032

AMELIORATION OF HUMAN ERECTILE DYSFUNCTION BY TREATMENT WITH INOS, INDUCERS OF INOS OR INOS CDNA

FIELD

This invention relates to a treatment of erectile dysfunction, and more specifically to the treatment of erectile dysfunction by use of inducible Nitric Oxide Synthase (iNOS) agents, including iNOS, inducers of iNOS, iNOS cDNA and recombiant iNOS cDNA-transformed penile smooth muscle cells (iNOS engineered cells), for the purpose of ameliorating vasculogenic dysfunction in the penis. The iNOS is preferably induced in vivo e.g., in penile corpora cavernosa, to produce penile tissue specific expression of increased levels of iNOS for amelioration of the patient's condition. Or iNOS may be induced in vitro in excised and cultured corpora cavernosa cells, extracted, purified and thereafter provided to patients in a wide variety of delivery systems. Alternatively, recombinant iNOS can be synthesized in vitro and delivered to the patient for treatment. cDNA iNOS may be introduced in patent penile tissue to produce recombinant iNOS in vivo. In another alternative the in vitro cultured cells can be transformed with penile iNOS cDNA and the resultant genetically engineered cells as introduced into the corpora cavernosa in vivo.

BACKGROUND

Impotence, the inability to obtain or maintain a penile erection sufficient for sexual intercourse, afflicts more than 12 million men in the USA. It is associated with aging and occurs in 25% of men aged 65, and 55% of men aged 75, irrespective of the fact that the libido of the majority of these patients is relatively unaffected. Annually it results in more than 400,000 outpatient visits and 30,000 hospital admissions in the U.S. Surgical implantation of penile prosthesis increased from 19,000 in 1989 to 32,000 in 1989. Accordingly, the costs of treating impotence in 1989 is conservatively estimated at 250 million dollars. In human terms, although impotence is not usually a life-threatening situation, its consequences for the patient and his partner are psychologically very serious.

Contrary to earlier assumptions in the literature, as much as 90% of impotence is due to organic and not to psychogenic causes. Despite the fact that aging is a predisposing factor, organic impotence may be present as early as puberty in some patients. Vasculogenic and neurogenic alterations leading to penile erectile dysfunction are at the root of the majority of the organic impotence syndromes, since male hormone disturbances and other possible physical causes of loss of the libido play a minor role in these problems.

Vascular disease of many causes will eventually lead to impaired penile erection. Thus, atherosclerosis, hypertension, diabetes, heavy smoking and alcoholism are all recognized risk factors for erectile dysfunction. Diabetics as a group are the most prone to vasculogenic impotence with more than 50% incidence in a population of about 2.5 million in the USA.

This invention is based on the discovery that effective ameliorative treatment can be based on inducing the penile tissue specific expression of nitric oxide synthase, the enzyme which synthesizes the compound nitric oxide (NO), which in turn functions as a mediator of penile erection.

The physiology of normal erection can be divided into three distinct processes acting in concert: (a) increased arterial inflow; (b) decreased venous outflow; (c) active cavernosal smooth muscle relaxation. The latter appears to be the key event, but the penile blood vessel hemodynamics is also mediated by the smooth muscle of the arterial tree. Accordingly, active smooth muscle relaxation in the penile artery and sinusoids is considered to be the pivotal step in generating a normal erection. Abnormalities in penile smooth muscle function may be the critical site in erectile dysfunction.

In a normal erection the stimulation is transmitted to the penis through the nervi erigentes, the pelvic autonomic nerve fibers. Neurotransmitters are released from three systems:

(a) norepinephrine from the sympathetic adrenergic fibers;

(b) acetylcholine from the parasympathetic cholinergic fibers; and (c) a substance from the nonadrenergic-noncholinergic (NANC) fibers. The NANC neurotransmitter has been shown to be nitric oxide (NO) and to act upon the smooth muscle to cause relaxation.

The smooth muscle relaxation of the trabeculae surrounding the lacunar spaces of the corpora cavernosa has three important functions: (a) reduction of the normally high resting (flaccid) resistance to arterial flow, thus increasing this flow through the helicine arteries into the endothelium-lined lacunar spaces; (b) regulation of blood storage into the penis, allowing penile engorgement; and (c) transmission of approximately 80% of systolic blood pressure into the cavernosal space. The latter will compress the draining venules that run in parallel between the expanding smooth muscle and the tough inelastic tunica albuginea, resulting in venous outflow restriction. Detumescence occurs by a reversal of this process, that is, an increase of the tone of the smooth muscle in both compartments leading to reduction of arterial inflow and the size of the lacunar spaces, followed by venous runoff.

NO and the endothelium-derived relaxing factor (EDRF) appear to play multiple roles in different biological processes. NO is considered to be responsible for the vasodilator activity of EDRF which is released from the endothelial lining of blood vessels and induces different effects in hypoxia, vascular disease, septic shock, and inflammation. EDRF plays a significant physiological role in the maintenance of vascular tone by inducing locally the relaxation of the smooth muscle cells. Our work has shown that in the penile corpora cavernosa, NO may be the NANC neurotransmitter in the penis and the main compound responsible for erection.

In the case of the penis, we have previously demonstrated by electric field stimulation (EFS), pharmacological treatments and the use of specific NOS inhibitors, that NO is the main mediator of penile erection in the human, dog, rat, and rabbit. A number of other laboratories have confirmed and extended these findings, by applying essentially two approaches: a) relaxation of corpora cavernosa strips in organ bath; b) erectile response in animal models. The latter procedure has been employed by us in a rat model to define the main object of this invention.

One of the sites of NO release in the penis appears to be at the non-adrenergic non-cholinergic (NANC) nerve terminals of the corpora cavernosa, from where it then binds to guanyl cyclase in adjacent cells and stimulates the formation of cGMP mainly in the smooth muscle target tissue. This cGMP synthesis in turn results in a decrease in intercelluar $Ca^{2+}$ and subsequent smooth muscle relaxation and penile vasodilation.

It is known in the art that Nitric Oxide Synthase (NOS) is the enzyme catalyzing the formation of NO in endothelial cells, macrophages, brain, liver and several other cell types and tissues. There are two types of NOS: constitutive NOS (cNOS), whose levels do not appear to change upon different experimental conditions; and inducible NOS (iNOS), whose synthesis can be stimulated by bacterial toxins and certain growth factors. In general, cNOS is present in brain (one isoform of which is known as neural NOS, or nNOS), and in endothelial cells, while iNOS is contained in macrophages, lung, liver, smooth muscle cells from large arteries and also in endothelial cells.

cNOS and iNOS isolated from different tissues show the existence of several isoforms within each group with specific cofactor requirements, mRNA sizes, and immunological properties. (The different type designations are shown below in parenthesis.) Within the cNOS group, characterized by their $Ca^{2+}$ dependence, there are three different cytosolic isozymes: (Ia), present in the brain, cerebellum, neuroblastoma cells; (Ib), present in endothelial cells; and (Ic), present in neutrophils. The first two are calmodulin dependent, and the third is calmodulin independent. Ib does not have $BH^4$ and FAD as cofactors, and Ia is the only one using FMN additionally as cofactor. There is also a particulate $Ca^{2+}$/calmodulin dependent isoform that makes up over 90% of endothelial cell cNOS.

Within the iNOS group (all $Ca^{2+}$/calmodulin independent with unknown regulators), a soluble type is present in the macrophages (II), hepatocytes, Kupfer cells, fibroblasts, endothelial cells, lung and liver, and has all the requirements of isoform Ia. A different particulate type (IV) is present in the macrophages and is only NADPH dependent. Recently, a new nomenclature has been proposed based on three NOS types: "I" or neuronal cNOS (nNOS) which is the brain cNOS; "II" or endothelial NOS (eNOS); and "III" or inducible NOS (iNOS).

Further evidence for the significant difference between cNOS, nNOS and iNOS is evident from the difference in their respective kinetics and substrate/cofactors requirements. L-arginine and NADPH are the common substrate and cofactor respectively. As noted above, the cNOS/nNOS and iNOS isozymes can be distinguished in that cNOS/nNOS is $Ca^{2+}$/calmodulin dependent, while iNOS is stimulated by tetrahydrobiopterin. NOS activity is inhibited by a series of competitive inhibitors such as $N^G$-nitro-L-arginine and $N^G$-methyl-L-arginine, or by NO chelators, such as hemoglobin. (3-H)citrulline synthesis is increased in certain cells by N-methyl-D-aspartate (NMDA) and glutamate. L-nitroarginine is 1000-fold more potent inhibitor of the cNOS than of the iNOS. Hydroxy-arginine and arginine dipeptides are also NOS substrates. Aminoguanidine appears to be a preferential inhibitor for iNOS, but its specificity varies with the cell type.

In addition, NOS mRNA (and resulting cDNA) are proving to be highly species and tissue specific. For example, the DNA sequence (including introns and exons) of the gene for rat brain cNOS (nNOS) has been cloned. Its mRNA is expressed as a 10.5 kb polynucleotide species. But the same mRNA species is not found in rat kidney, liver, skeletal muscle or heart tissue. Besides rat cerebellum, cNOS has been purified from rat polymorphonuclear neutrophiles. The cNOS cDNA has also been cloned from bovine and human endothelium. In the latter case, the corresponding cNOS mRNA is 4 kb in length, and is encoded by a gene different from that expressed in the brain. Further, iNOS has been purified from LPS-stimulated rat and mouse macrophages, rat vascular smooth muscle, human hepatocytes and condrocytes. Induction of NOS is triggered in vivo by injection of lipopolysaccharide from E. Coli (LPS), and in vitro by incubation of cells or tissue strips with LPS, interleukin β, and tumor necrosis factor (TNF-α) interferon. The induction is protein synthesis-dependent and blocked with dexamethasone or other glucocorticoids, and with TGF-β.

The presence of NOS in the human, rabbit, and rat penis tissue homogenate has been shown by us by following the conversion of (3-H) L-arginine into (3-H) L-citrulline in the cytosol fraction, and others have detected the nNOS isoform in the nerve terminals of the penis by histochemistry and immunocytochemistry. However, no characterization has yet been made of the main penile NOS isozyme responsible for NO synthesis during sexual stimulus. In addition, recent gene knock-out experiments failed to affect the reproductive behavior of transgenic mice when nNOS was silenced. Our own current work indicates the presence of distinctive penile NOS isozymes different from those in other tissues. Other non-NOS dependent pathways may be present in the penis and they are supposed to cooperate during penile erection with the NO cascade, or become predominant after a long-term impairment or silencing of the penile NOS. These putative physiological ancillary relaxants of the penile smooth muscle include vasoactive intestinal polypeptide (VIP), calcitonin gene related polypeptide (CGRP), prostaglandins, etc.

That NOS decrease or inactivation may be associated with certain forms of erectile dysfunction has been shown by our recent work on aged intact rats, diabetic BB rats, and castrated rats. In both intact senescent rats and castrated rats, the levels of erectile response to EFS and of penile NOS can be restored to normal values by androgen administration. EFS itself modulates penile NOS activity, and it does this in a differential form between intact and castrated rats.

However, no treatment based on the manipulation of endogenous NO synthesis or of NOS activity or expression has been proposed in the literature. The current pharmacotherapy of erectile dysfunction is based exclusively on the topical application or the direct intermittent self-injection into the penile corpora cavernosa of mixes of vasoactive compounds, including nitrodonors, immediately prior to sexual intercourse, or surgical treatments based on prosthesis implantation or arterial/venous operations. For example, U.S. Pat. Nos. 4,931,445 (Goldstein et al.), 5,336,678 (Cavallini), and 5,278,192 (Fung et al.), teach methods of treating impotence through administering the drugs etoparidone, Minoxidil, or isobutyl or isoamyl nitrite, respectively. Bredt et al. in U.S. Pat. No. 5,268,465 have characterized a rat brain cDNA encoding a calmodulin-dependent NOS molecule of specific sequences, but does not suggest or teach treatment of erectile dysfunction therewith. This appears to be a cNOS or nNOS. Stuehr et al. in U.S. Pat. No. 5,132,407 teach a three-component calmodulin-independent cNOS flavoprotein purified from mouse macrophages, but does not teach treatment of erectile dysfunction.

Voss et al. in U.S. Pat. No. 4,801,587 teaches use of DMSO as an absorption agent to introduce papaverine, a compound known for treatment of human impotence. El-Rashidy in U.S. Pat. No. 5,256,625 teaches the use of hydroxy propyl-β-cyclodextrin as an absorption enhancer for papaverine.

The subject of the current invention, the penile iNOS isoform, has never been detected either at the enzymatic or protein levels, at the mRNA levels, nor in penile tissue sections by immunocytochemical procedures. Other than our own work on rat penile smooth muscle cells (RPSMC) described herein there are no in vitro reported studies on iNOS detection in cultures of penile cells. It is presently unknown whether penile iNOS has any physiological role, and there are no publications suggesting that it could be applied for the therapy of erectile dysfunction. In fact, vascular iNOS in general, when induced, may have a deleterious effect on blood pressure. It is assumed to participate in septic shock, without apparently acting on the normal maintenance of blood vessel tone. In addition, the induction of iNOS to improve penile erection has not probably been considered before because of the risk of systemic hypotension or uncontrollable priapism. To our knowledge, no publications on the continuous delivery of compounds into the penis are available.

Accordingly, there is a need in this field to provide an improved method of treatment of erectile dysfunction by inducing endogenous production of iNOS in penile tissue or by introduction of exogenous iNOS to penile tissue.

THE INVENTION

Objects

It is among the objects of this invention to provide methods and compositions for amelioration of erectile dysfunction through local treatment of the penis with iNOS, inducers of iNOS and iNOS cDNA in order to minimize the systemic effects.

It is another object of this invention to provide methods and compositions for increasing the level of iNOS in patient penile tissue through introduction of iNOS into the tissue.

It is another object of this invention to provide delivery systems for introduction of inducers of iNOS into the penile tissue of patients for the purpose of ameliorating vasculogenic impotence.

It is another object of this invention to provide methods of treating human patients exhibiting erectile dysfunction symptoms by a variety of systems, including penile implantation of microcapsules containing iNOS inducers or penile iNOS recombinant protein (native or modified) in the corpora cavernosa or by genetically engineering production of iNOS in affected penile tissue.

Still other objects of this invention will be evidence from the Detailed Description, Drawings and claims.

BRIEF DESCRIPTION OF DRAWINGS

The invention is described in more detail by reference to the drawings in which:

FIG. 11 shows that a suboptimal dose of a nitric oxide synthase inhibitor differentiates respondents from non-respondents in the EFS erectile test in rats of different ages;

FIG. 12 shows the increase in nitric oxide synthase activity in the penile cytosol of rats treated for one week with inducers of nitric oxide synthase;

FIG. 13 shows that the increase in NOS activity in the cytosol of inducer treated rats is inhibited by treatment with L-NAME but is unaffected by treatment with aminoguanidine; and FIG. 14 shows the NOS activity in the penile tissue of inducer treated rats as detected by immunochemistry.

SUMMARY

The present invention provides a new treatment for erectile dysfunction by the mechanism of raising the level of inducible nitric oxide synthase (iNOS) in the penis by various agents, which in turn, in vivo, effectuates the production of nitric oxide (NO) to mediate the erectile response by its effect in relaxing the smooth muscle in the corpora cavernosa of the penis.

This invention is directed to methods and compositions for ameliorating erectile dysfunction in patients through increasing levels of iNOS in penile tissue either by direct introduction of iNOS to penile tissues, or, in the presently preferred embodiment, inducing endogenous production of iNOS by treatment with appropriate iNOS inducers, introduction of iNOS cDNA or by transformation of excised and cultured penile corpora cavernosa cells with recombinant iNOS cDNA and re-introduction of these cells in the penis in vivo where they proliferate, and rejuvenate and augment the iNOS-producing capability of the corpora cavernosa tissue.

Figure 1:
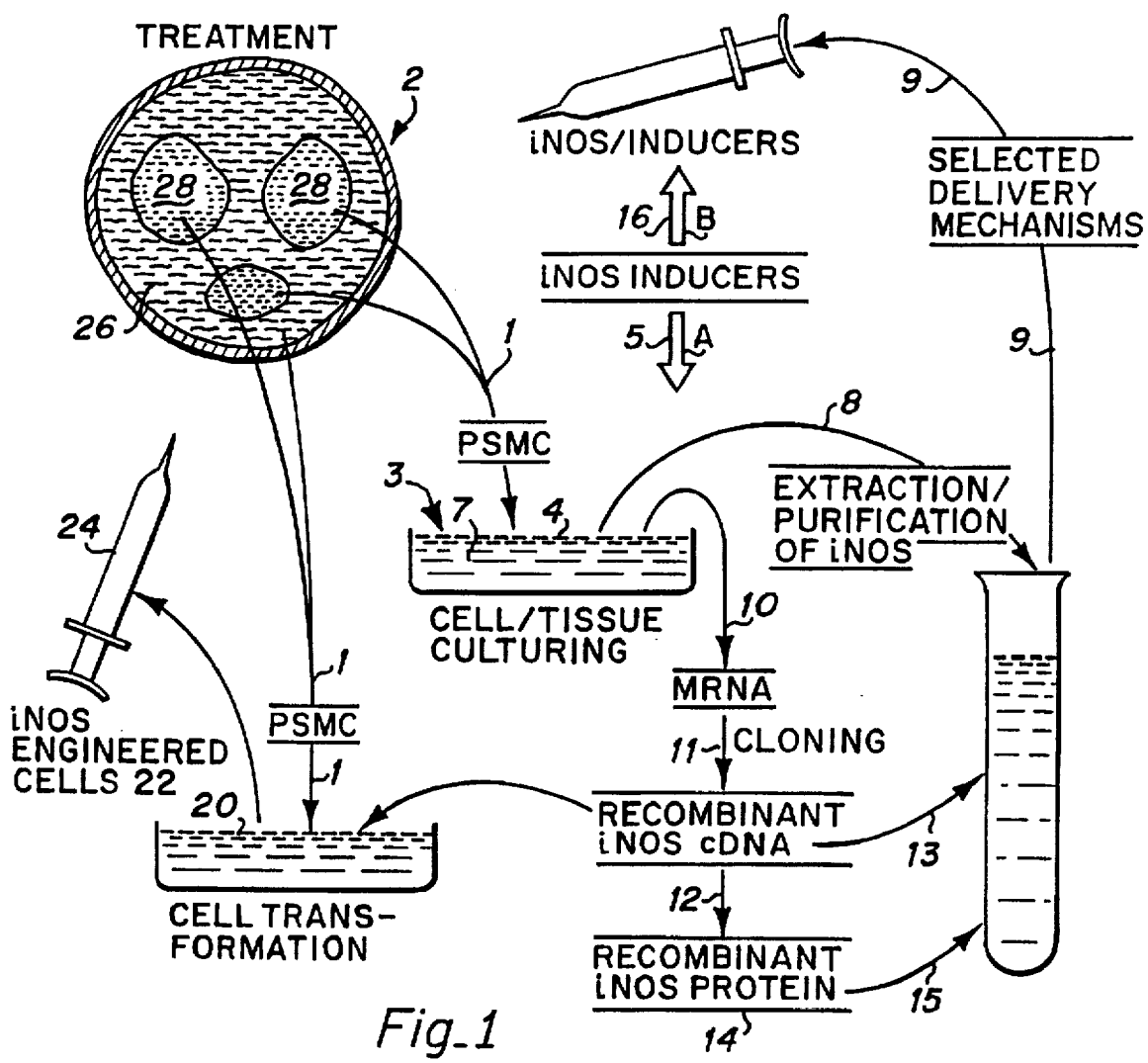
FIG. 1 is a schematic illustration of the methods of the invention including use of iNOS and iNOS inducers directly or indirectly to treat human erectile dysfunction.

FIG. 1 shows schematically the several embodiments of the invention. In one embodiment, cells from excised tissue specimen 1 (preferably corpora cavernosa cells) from penis 2 are cultured 3 in appropriate media. The cultured Penile Smooth Muscle Cells (PSMC) 4 are then treated with inducers 5 appropriate for in vitro induction of iNOS. The iNOS 7 from the induced cells 4 can be extracted, purified 8 and delivered 9 to the penis 2 for treatment. Alternatively, the mRNA from in vitro induced PSMC can be isolated 10 and its corresponding cDNA cloned 11, e.g., by RT/PCR (reverse transcription and polymerase chain reaction), library techniques, or other cloning techniques. The resulting cDNA 12 is extracted 13 and delivered 9 to the penis of a patient for treatment. Alternatively, the cloned iNOS cDNA 12 can be used to generate recombinant iNOS protein 14 which can be recovered 15 and delivered 9 to the penis 2 for treatment. In yet another embodiment, the cultured PSMC cells 20 are transformed with the recombinant penile iNOS cDNA 12 to produce iNOS engineered cells 22 which are then introduced 24 into appropriate penile tissue 26, such as the corpora cavernosa 28. There the cells proliferate to rejuvenate and augment the endogenous iNOS producing capability of the penile cells and tissue structures.

In the preferred embodiment, inducers 16 appropriate for in vivo induction of iNOS can be delivered 9 to the penis 2 of the patient thus raising the level of iNOS endogenously produced in the penile tissue.

In vitro induction of iNOS in the cultured Rat Penile Smooth Muscle Cells (RPSMC) was accomplished by treatment with different agents alone and in combination, such as lymphokines and bacterial lipopolysaccharide (LPS). Treatment with various inducer mixes caused significant increases in the NOS activity of the treated cells as measured by the accumulation of nitrites in the culture medium. The time-course showed a linear response up to at least 60 hr, which was inhibited by L-NAME thus indicating that this increase in nitrite release is due to iNOS induction. The fact that the observed stimulation of nitrite accumulation in the RPSMC culture medium was due to iNOS induction was confirmed by demonstrating the presence in the induced penile cells of both iNOS mRNA and iNOS protein by northern and western blotting respectively. The probe used for northern blot analysis was a 350 bp fragment of iNOS cDNA from RPSMC; western blot analysis was by reaction of lysed induced RPSMC with a commercially available iNOS antibody.

Based on our results on the conditions for in vitro induction of cultured cells, treatment in vivo is accomplished by delivering an inducer mix, such as the one described in detail in Example 2 below comprising $E. coli$ lipopolysaccharide (LPS), recombinant rat interferon-θ (IFN-γ), recombinant human tumor necrosis factor (TNF-α), and recombinant human interleukin-1 β (IL-1β), to the penile corpora cavernosal tissue of a patient. Other mixes may be used and added to the delivery of single agents. A delivery method involving constant infusion of the inducer mix by means of an osmotic pump attached to a catheter which feeds into the corpora cavernosal tissue is the presently preferred method, although any suitable delivery system can be employed, such as embedded or injected microcapsules, injection of the mix, topical or subdural application, or the like.

The disclosed pump system can be set to deliver the inducer mix for a short period (e.g., 1 ul/hr during 3 days) or for a longer treatment period (e.g., 0.5 ul/hr during 14 days). We have observed that the short-term (ie., 3 day) treatment is more efficacious than the long-term (ie., 14 day) treatment, however this may be an artifact, due to the inactivation of some of the biological constituents in the inducer mix when the mix remains in the pump for extended periods. The formulation, delivery system, and scheduled administration is adjusted for the human patient on a case by case basis.

The described treatment with iNOS inducers markedly improves the erectile response in in vivo tests performed on rats of three different age groups, adult (5 month old), "old" (20 month old), and "very old" (28–32 month old). The erectile responses of the subject rats after completion of the inducer treatment were measured by detecting the maximal intracavernosal pressure in response to electrical field stimulation (EFS) of the cavernosal nerve in the animals.

Treatment with a sub-optimal dose of the nitric oxide synthase inhibitor N-nitro-L-arginine methyl ester (L-NAME) subsequent to treatment with the inducer significantly reduced the observed erectile response. This data demonstrates that the inducer treatment's mechanism is via the NOS cascade. That the inducer treatment works by induction of nitric oxide synthase is further demonstrated by data that the penile tissue homogenates of rats treated with inducers of iNOS showed increased NOS activity relative to untreated controls and by histochemical detection of NOS activity in penile tissue sections.

DETAILED DESCRIPTION OF THE BEST MODE

The following detailed description illustrates the invention by way of example, not by way of limitation of the principles of the invention. This description will clearly enable one skilled in the art to make and use the invention, and describes several embodiments, adaptations, variations, alternatives and uses of the invention, including what we presently believe is the best mode of carrying out the invention.

Measurement of NO production (half life: 5 sec) is based on a direct spectrophotometric estimation of its reaction with oxyhemoglobin. Alternatively, NOS activity can be determined from the generation of NO co-products, such as (3-H) citrulline originated from (3-H) L-arginine, or from the relatively stable NO metabolites, such as nitrites and nitrates. The latter procedure is particularly suitable for measuring the release and accumulation of nitrites and nitrates in the extracellular medium.

The determination of cGMP provides an indirect way to follow NO synthesis, due to the effects of the latter on guanylate cyclase. This modulation leads to an increase in the levels of cGMP, with the subsequent intracellular free $Ca^{2+}$ reduction, which is considered to be the probable trigger for smooth muscle relaxation.

EXAMPLE 1

In vitro Induction of iNOS in Smooth Muscle Cells

This example demonstrates the method for obtaining a high level of stable induction of nitric oxide synthase in vitro in cultures of rat penis smooth muscle cells (RPSMC), to select conditions for the in vivo experiments.

Primary cultures of RPSMC were initiated from small pieces of penile tissue excised from 3 months old Sprague Dawley rats, utilizing Dulbecco's modified Eagle medium (DMEM) with 20% fetal calf serum, at 37° C. in the presence of 5% $CO_2$. Cells grown from the explants were then transferred to medium with 10% serum, and at the 4th to 10th passage (1:3 splits) they were utilized for the experiments, unless otherwise indicated. Alternatively, cells from the 4–8th passage stored under liquid nitrogen were used to reinitiate the cultures, and used for incubations on the following 2–4 passages. These cultures are considered to consist mainly of smooth muscle cells from the penis based on morphological and cytoimmunochemical criteria.

All experiments were conducted at 90–100% cell confluence on "Primaria" cultureware, usually 24-well plates, adding or not the inducers indicated in each experiment.

When not specifically stated, the standard binary induction mix consisted of bacterial lipopolysaccharide (LPS) (10 ug/ml) and recombinant murine interferon-θ (INF-θ) (250 U/ml). Other substances to be tested were added as indicated to the serum-containing medium, and the incubation proceeded for the times indicated. The medium was always collected and stored for an indirect measurement of NO production based on the determination of its conversion into nitrites. The procedure was based on the application of the Greiss reagent, using 250 ul of the medium mixed with an equal volume of reagent. Each experimental condition was carried out in triplicate.

Figure 2:
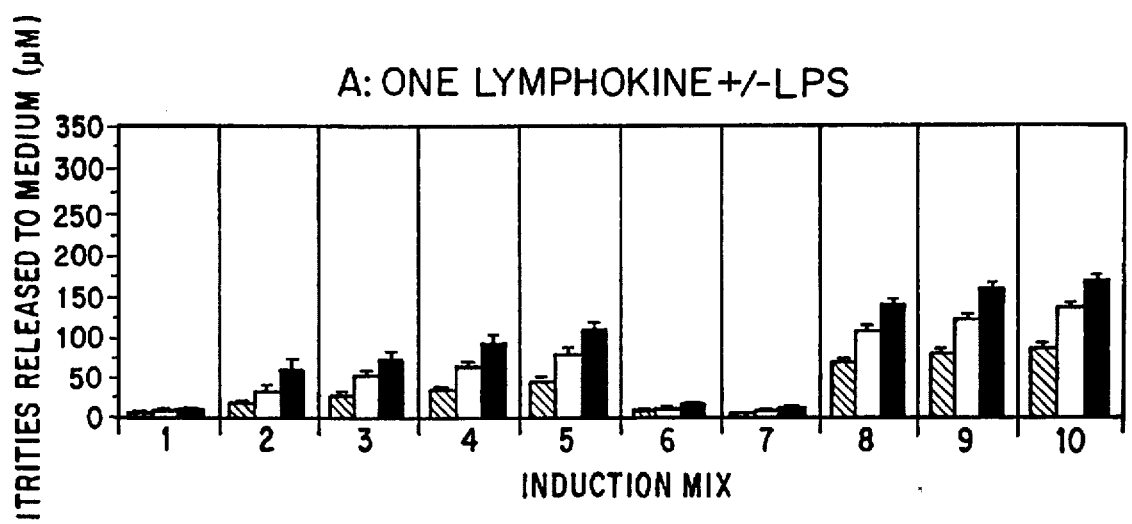
FIG. 2 shows the in vitro stimulation of nitric oxide synthesis in cultures of rat penis smooth muscle cells (RPSMC) by treatment with iNOS inducer mixes comprising one lymphokine supplemented with and without bacterial lipopolysaccharide (LPS) as measured by the accumulation of nitrites in the culture medium.

FIG. 2 presents the results obtained in 48 hr incubations with one cytokine supplemented or not with LPS. In the absence of inducers (panel 1, left bar) there is only a very marginal NO production (less than 5 uM, or 2.5 nmoles per well), and LPS by itself (1 and 10 ug/ml) only marginally stimulate this basal synthesis by less than 50% (panel 1, central and right bars, respectively).

The addition of INF-θ (50 to 500 U/ml) in the absence of LPS (panels 2 through 5, left bar) causes a dose-proportional moderate increase of nitrites to a maximum of 45 uM. Supplementation with 1 or 10 ug/ml LPS (central and right bars, respectively) stimulates the induction up to 120 uM, or nearly 20-fold the basal level. In contrast, TNF-α up to 500 u/ml did not have any effect either in the presence or the absence of LPS (panels 6 and 7). Interleukin-1β (IL-1β) at the minimum concentration tested (5 ng/ml) in the presence of 10 ug/ml LPS (panel 8, right bar) was slightly more effective than the 500 U/ml dose of INF-θ (panel 8, right bar), but higher concentrations of IL-1β up to 100 ng/ml (panels 9, 10), enhanced relatively little the level of stimulation.

Figure 3:
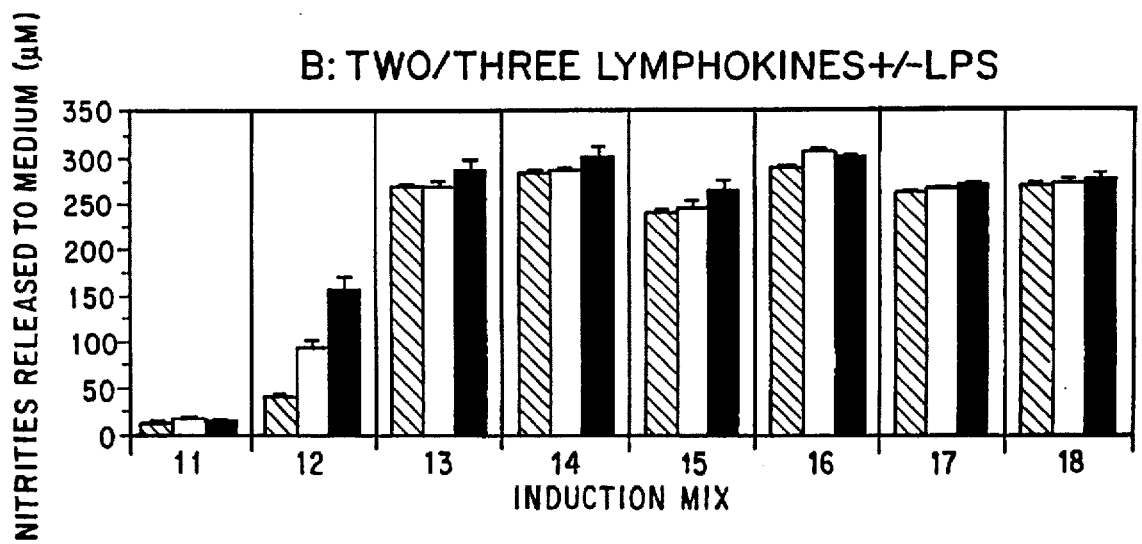
FIG. 3 shows the in vitro stimulation of nitric oxide synthesis in cultures of RPSMC by treatment with iNOS inducer mixes comprising two or three lymphokines plus LPS as measured by the accumulation of nitrites in the culture medium.

The supplementation of the INF-θ/LPS binary combination with additional cytokines (tertiary or quaternary mixes) is presented on FIG. 3. The basal NO synthesis in this experiment in the absence of cytokines (panel 11) was slightly higher than in the previous series (compare with panel 1), and the same occurs with the binary combination of 10 ug/ml LPS and 250 U/ml INF-θ (panel 12 compared with panel 5), chosen as "standard mix" for successive in vitro experiments because of its low cost. Taking this mix as reference, the addition of TNF-α to 500 U/ml and IL-1β (panel 13) doubles NO synthesis in the presence of LPS (central and right bars). Moreover, what is very important, the iNOS induction becomes independent of LPS addition (left bar). No further stimulation is achieved by raising TNF-α to 3,000 U/ml (panel 14).

That TNF-α is not the essential ingredient is corroborated by: (a) omitting it from the mix and raising IL-1β to 100 U/ml, which only slightly decreases stimulation (panel 15), and by (b) supplementing the latter mix with 500 U/ml TNF-α, which although prevents this small reduction does not raise the stimulation further (panel 16), IL-1β can be lowered to 5 ng/ml and IFN-γ to 100 U/ml (panel 17) with little effect on the induction (compare with panels 14 and 16). The possibility of reducing IL-1β to 5 ng/ml without compromising stimulation is very obvious by comparing panel 18 with the homologous panel 13 where four fold more IL-1β was used.

Figure 4:
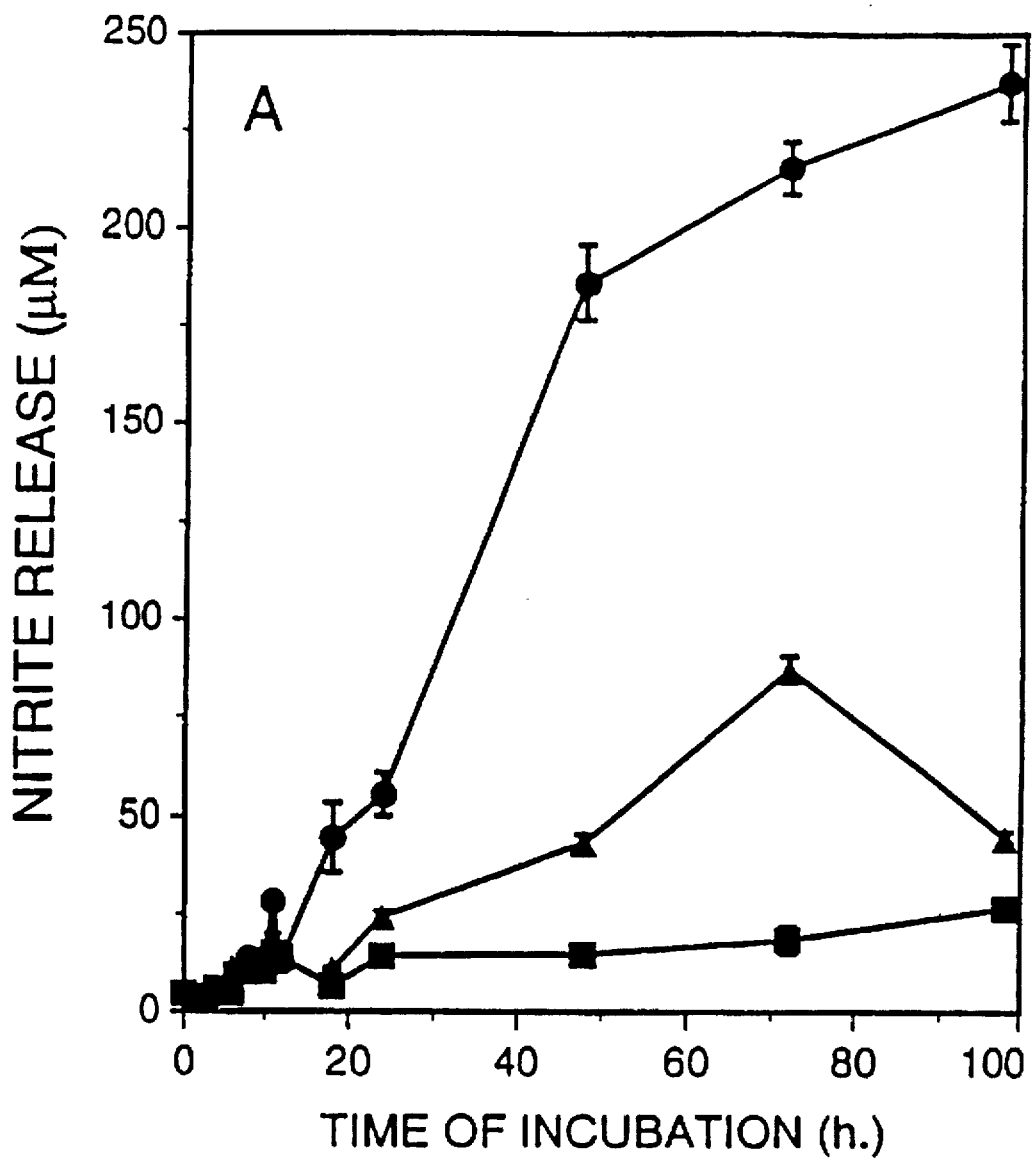
FIG. 4 shows the time course and stability of the iNOS induction of RPSMC cultures treated with the standard binary iNOS inducer mix, in the presence or absence of the NOS inhibitor L-NAME as measured by accumulation of nitrites in the culture medium.

The time-course of the iNOS induction is shown on FIG. 4, where cultures of RP-SMC were treated or not with the standard mix, in the presence or absence of a NOS inhibitor (L-NAME), for periods ranging from 0 to 96 h and nitrites were estimated in the medium. In the absence of an inhibitor there is very little nitrite accumulation even at 96 h (solid squares), but with the standard induction mix, after a 6–10 h lag period of little stimulation, there is a nearly linear synthesis up to 48 h, with a slow-down in this rate after that period (solid circles). That this nitrite release is due to iNOS induction is shown by the up to 85% inhibition obtained with 2 mM L-NAME (solid diamonds).

Figure 5:
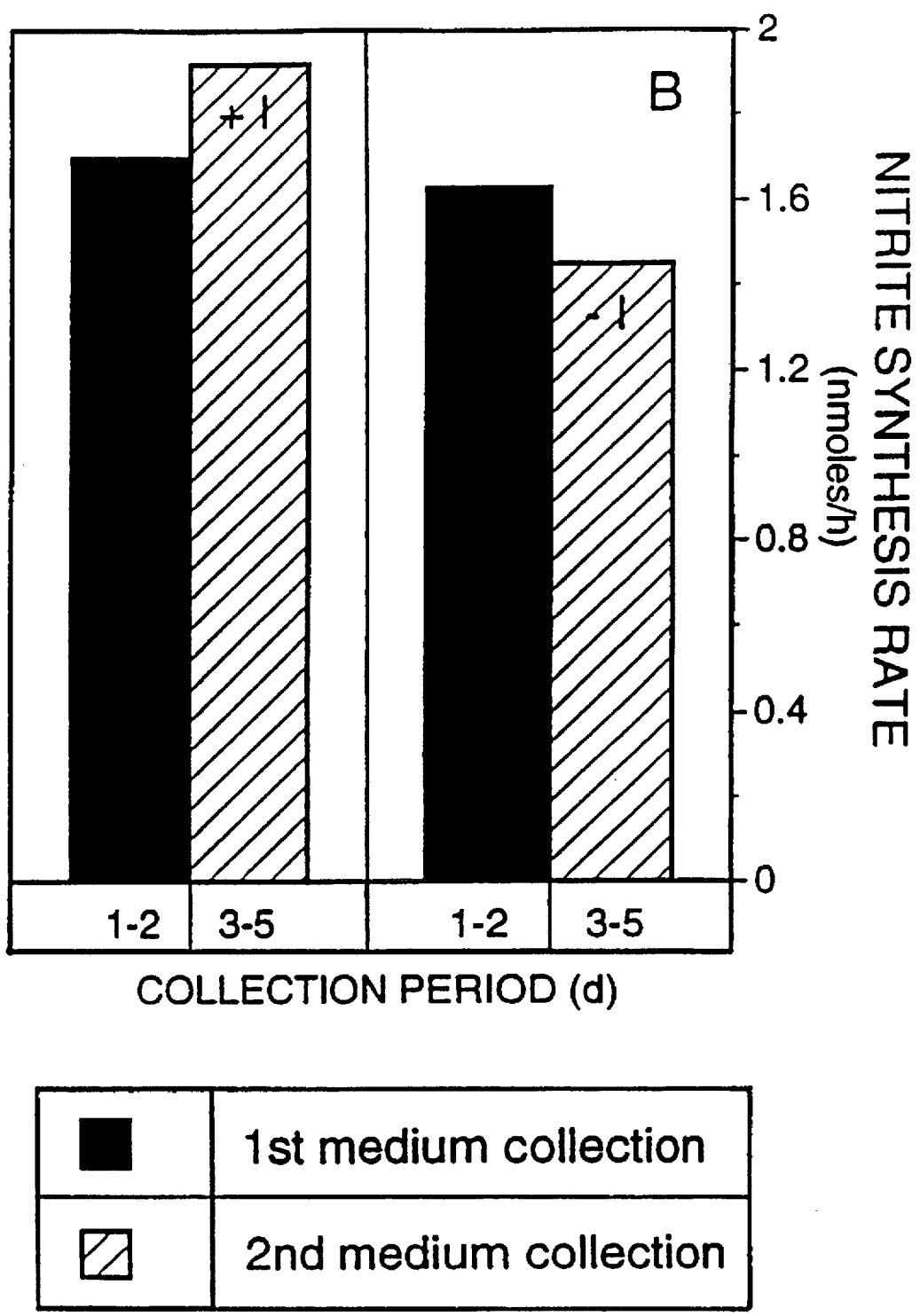
FIG. 5 shows that the turnover of the enzyme when the inducers are removed and not replaced is slow thus indicating the persistence of high levels of iNOS for a considerable period after induction.

The slow-down of nitrite synthesis after 48 h in the presence of inducers is not due to a significant increase in iNOS degradation but rather to feed-back inhibition of enzyme activity by excessive product accumulation, as shown on FIG. 5 (+I). RP-SMC were cultured to confluence onto 24-well plates in the absence or presence of inducers, and medium was removed at 48 h and replaced by fresh medium containing inducers or not. When nitrite synthesis is prorated per hour, the value obtained during days 3–5 (hatched bar) is even higher than that occurring in the preceding two days (empty bar). The turnover of the enzyme when the inducers are removed at 48 h and not replaced (FIG. 5 (−I)) seems to be slow, which should assure the persistence of high iNOS levels for a considerable period after ceasing the induction.

The fact that the observed stimulation of nitrite accumulation in the RPSMC culture medium was due to iNOS induction was confirmed by demonstrating the presence in the induced penile cells of both iNOS mRNA (northern blots), and iNOS protein (western blots). For northern blot analysis of iNOS mRNA expression, mRNA was isolated from RPSMc on two 10 cm dishes by standard guanidium thiocyanate/CaCl method complemented with two series of phenol/chloroform extractions separated by ethanol precipitation, and polyA+ RNA was isolation by oligo dT chromatography. Northern blots were done with 3–4 ug poly A+ RNA per lane on formaldehyde-denaturing 1% agarose gels, and subsequent transfer to the nylon membranes with 10X SSC, using the Posiblot pressure blotter.

Filters were hybridized as we previously described with a [32-P] labelled specific probe consisting in a 350 bp fragment of iNOS cDNA from RPSMC, designated RPSMC-iNOS350. This fragment was generated by us by reverse transcription (RT) of 1 ug of polyA+RNA from RP-SMC induced with LPS/γINF, using antisense and sense primers NO4 and NO3, respectively. These primers are 20-mers designed from the nucleotide sequence of the mouse macrophage iNOS and encompass a 350 hp fragment in the FMN region of this cDNA. This probe was cloned into Invitrogen PCRII vector and subcloned into Promega pGem3z. Automated dideoxysequencing showed this probe to have 92% homology, respectively, to the mouse macrophage iOS cDNAs. After treatment with the NOS probes, northerns were re-hybridized with the glyceraldehyde phosphate dehydrogenase (GPDH) probe.

For western blots, other RPSMC dishes submitted to the induction were washed, lysed in a conventional buffer, boiled for 5 min, and the extracts clarified in a microcentrifuge. Aliquots were ran on an SDS electrophoresis minigel with the appropriate molecular weight standards and submitted to a western blot transfer to nitrocellulose membranes. The filters were reacted with a 1/2000 dilution of a commercial rabbit antiserum against the carboxi terminus of the mouse macrophage iNOS (Affinity Bioreagents). The signal was visualized by a horse radish peroxidase goat anti-rabbit secondary antibody and a commercial ECL (luminol) detection kit.

Figure 6:
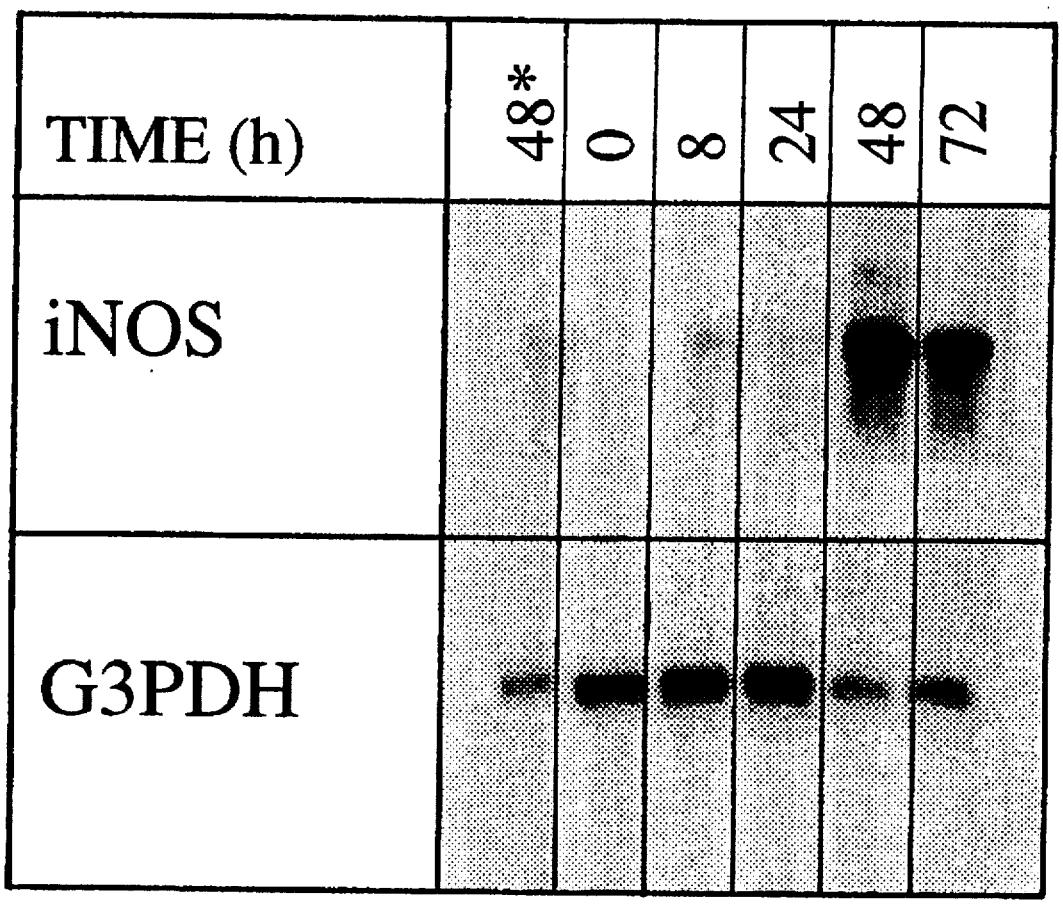
FIG. 6 shows the northern blot of poly A+ mRNA from RPSMC submitted to a time-course of induction, as hybridized with a RPSMC iNOS probe.
Figure 7:
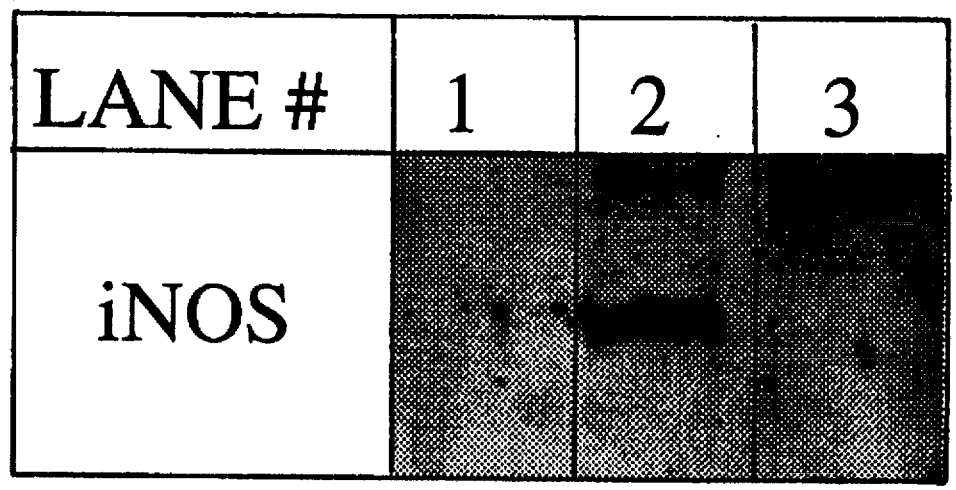
FIG. 7 shows the western blot of an extract obtained by lysis of induced RPSMC and reacted with commercial iNOS antibody.

FIG. 6 shows the northern blot of polyA+ from RPSMC submitted to a time-course of induction, as hybridized with our rat PSMC iNOS probe. The 4 kb typical signal is visible on the top part, and the glyceraldehyde phosphate dehydrogenase reference band on the bottom part. FIG. 7 shows the western blot of an extract obtained by lysis of induced RPSMC and reacted with a commercial iNOS antibody, indicating the expected 125–130 KD iNOS band (lane 2). No signal was obtained with a rat cerebellum extract (lane 1). Lane 3 is empty.

EXAMPLE 2

Direct Infusion of iNOS Inducers into the Penile *Corpora cavernosa*

This example demonstrates the method for infusing inducers of nitric oxide synthase directly into the penis in a rat.

Male Fischer 344 rats from three age groups designated "adult" (5-month old), "old" (20 month old), and "very old" (28–32 month old) rats, were anesthetized with an intraperitoneal injection of sodium thiopental (pentobarbital) at 50 mg/kg. The definition of these age groups in terms of relative aging corresponds to conventional designations for the Fisher 344 strain of rats (maximal life span approximately 34–36 months; optimum breeding activity 2.5–8 months). The adult and very old rats were retired breeders whenever possible. Animals were maintained under controlled lighting and were treated according to NIH regulations. The number of animals in each group for each individual experiment is indicated in the corresponding figure.

A transversal suprapubic skin incision (5 mmm) was done to expose the penis angle and its proximal portion. The right corpora cavernosa was then cannulated with a 27-gauge needle attached to a vinyl tubing (Bolab/bb317–85 Arizona) which was connected with an ALZET$^R$ osmotic pump (Alza Corporation, Palo Alto, Calif.). Each pump (100 or 200 ul reservoir volume, as indicated) contained a mix of *E. coli* lipopolysaccharide (LPS) at 1 ug/ml, recombinant rat interferon-θ (IFN-γ) at 2,500 U/ml, recombinant human tumor necrosis factor-(TNF-α) at 2,500 U/ml, and recombinant human interleukin-1β (IL-1β) at 50 ng/ml.

The needle and the tubing were fixed to the penis peripheral tissues by Mersilene* 6-0 suture and the osmotic pump was placed subcutaneously on the rat abdomen. The needle was pierced into the corpora cavernosa, checking its proper delivery into the lacunar spaces by injection or heparinized saline solution and observation of the mechanically induced erection prior to the final connection with the pump. The incision was closed by layer using Dexon* Plus 4-0 suture and the success of the operation was checked all throughout the experiment by observation of a normal recovery and urinary activity. These criteria were completed by verifying the absence of peripheral hematomas or inflammation when the pump was removed. Each pump delivered the inducer mix by osmotic pressure through the catheter directly into the corpora cavernosa, either at 1 ul/hr during 3 days (pump 1003D) or at 0.5 ul/hr during 14 days (pump 2002).

In certain cases pump 1003D was removed from the anesthetized rat at the third day, and a new pump with fresh solution was instilled in the abdomen and connected to the catheter as above. The treatment proceeding until all the content of the reservoir was expelled, for an additional 3 days period.

EXAMPLE 3

Measurement of the Improvement of Erectile Response

This example demonstrates the method for measuring the improvement in erectile response caused by treatment with inducers of nitric oxide synthase.

At the completion of each treatment rats were anesthetized as in Example 1 and the erectile response was measured by a modification of a published procedure. Briefly, the cavernosal nerve was surgically exposed and stimulated with a square pulse stimulator connected to a platinum bipolar electrode positioned on the nerve. Through a needle inserted into the cavernosa, the intracavernosal pressure was recorded with a pressure transducer connected to a recorder that was calibrated with a manometer in order to express the response in mm of mercury. The animals were reinjected every 45 min with 35 mg/kg of ketamine for the whole duration of the experiment (about 2–3 hours).

Each rat was submitted to the following sequential treatments done in duplicate: a) electrical field stimulation (EFS) at a frequency of 15 Hz for pulses of 30 sec, separated for 5 min intervals, for the voltage response curve, at 15, 10, 2.5, 5 and 10 volts, in this order; b) EFS at 10 volts with the nitric oxide synthase (NOS) inhibitor N -nitro-L-arginine methyl ester (L-NAME) at 2 mg/kg, at a single dose per animal, recording 30 min. after injection. In some animals, the systemic blood pressure was measured at the beginning of the experiment, by intrafemoral cannulation and recording as above. Means and standard deviations were determined for the intracavernosal pressure values, and the statistical significance was obtained by the paired Student's t test.

Figure 8:
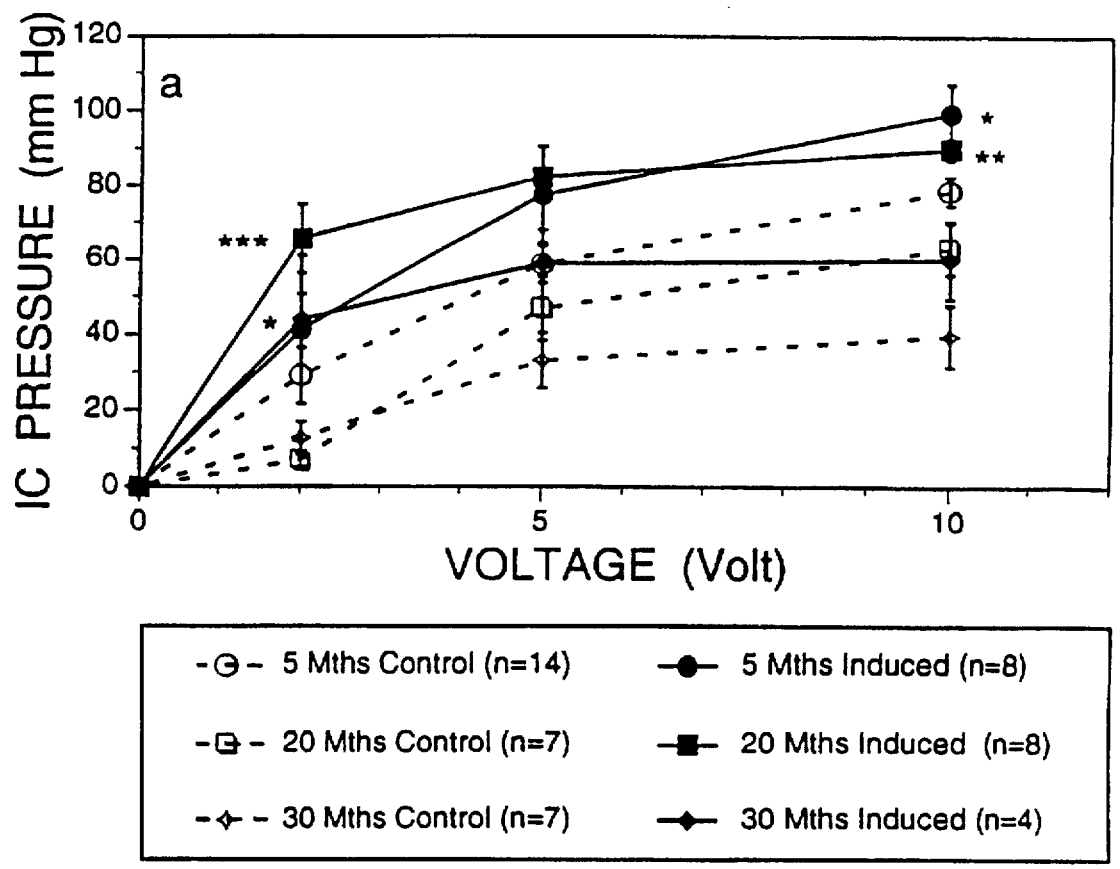
FIG. 8 shows the uniform improvement in erectile response electrical field stimulation of the cavernosal nerve in 5, 20, and 30 month old rats treated for three days with a constant infusion of several inducers of the inducible form nitric oxide synthase.

FIG. 8 shows that there is a significant increase of the erectile response to EFS measured by the maximal intracavernosal pressure at 10 volts in adult and old rats, but a non-significant stimulation in very old rats, treated for three days with the 100 ul pumps (open symbols), as compared with rats of the same ages not submitted to this treatment. At the 2 volt threshold the stimulation of erectile response is significant in all groups. Treatment of the old rats displaying erectile dysfunction with the iNOS inducer mix turns them into better respondents than the younger animals (adult group).

This considerable enhancement of penile erection found even in non-aged (adult) rats is not accompanied by undesirable side effects. The rats look healthy and alert, their systemic blood pressure remains normal, and there is no indication of priapism. This suggests that whatever the mechanism of penile erection enhancement, it remains under physiological control which is released by the EFS stimulus.

Figure 9:
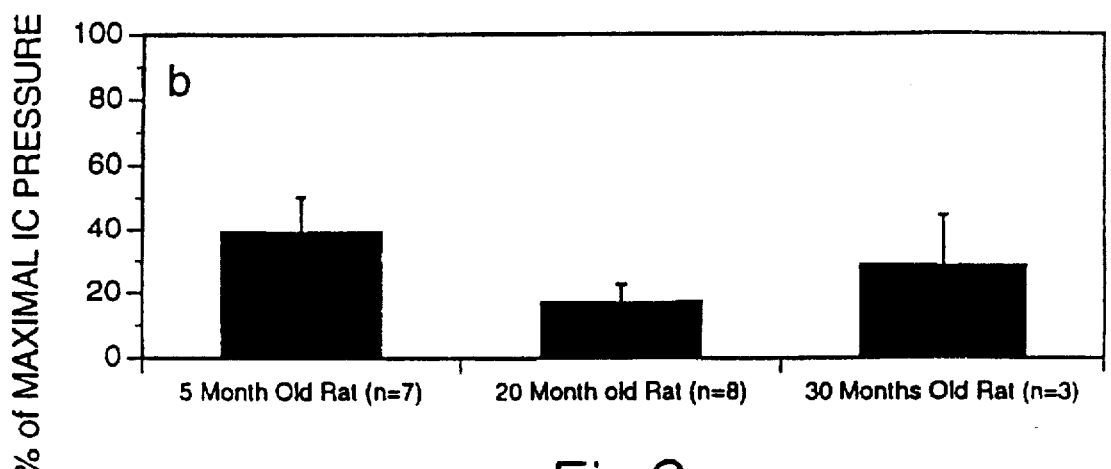
FIG. 9 shows the increase sensitivity of the erectile response to a suboptimal dose of an inhibitor of nitric oxide synthase of the rats treated in the experiment depicted on FIG. 8.

FIG. 9 shows that the stimulation of penile erection in the treated rats is dependent on the NOS cascade, since it is inhibited by sub-optimal doses of L-NAME. The fraction of maximal intracavernosal pressure remaining after L-NAME treatment was established and compared with equivalent values in untreated rats previously obtained by us in a separate study. The comparative values in the treated and untreated rats were: 39% vs 62% (adult), 18% vs 30% (old), and 28% vs 23% (very old), in the treated vs untreated rats. This indicates that in the adult and old animals the dependence on the NOS cascade upon treatment becomes even higher than in the absence of NOS inducers and in the senescent remains the same.

Figure 10:
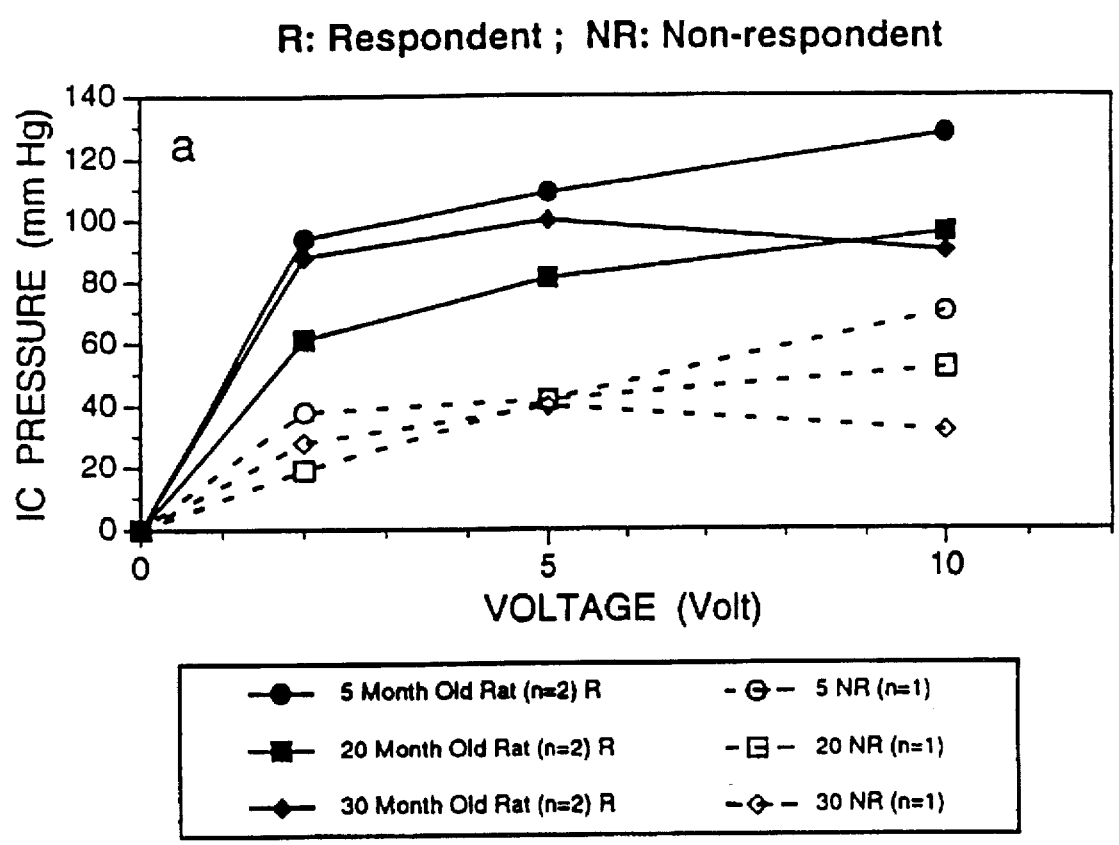
FIG. 10 shows that a medium-term local treatment (14 days) of three age groups with inducers of nitric oxide synthase does not give a better response than the short term paradigm in the enhancement of penile erection triggered by electrical field stimulation.

The efficacy of the short-term treatment (3 days) over longer treatments where the inducer mix remains in the pump for 14 days, with the possibility of inactivation of some of the biological constituents, is shown in the experiment depicted on FIG. 10. This illustrates the effects on the erectile response to EFS after the 14 days treatment with the same inducers used in FIG. 8. Two groups of rats are apparent in each age group: a) high respondents (solid symbols), with up to 50% and 300% stimulation of the intracavernosal pressure at 10 and 2 volts, respectively, above the respective untreated rats (shown on FIG. 8); b) non-respondents (open symbols), with values similar or below the untreated rats.

The success of a treatment with iNOS inducers can be judged by the sensitivity to a sub-optimal dose of L-NAME, as shown on FIG. 11. Even more evident than in the case of the experiment depicted on FIG. 9, L-NAME inhibited by over 95% the erectile response of the respondent animals in the three age groups, whereas in the non-respondent rats the inhibition was normal (as in the untreated rats).

EXAMPLE 4

Measurement of Increased NOS Activity After Inducer Treatment

This example demonstrates the method for showing that the improvement in erectile response is accompanied by the stimulation of nitric oxide synthase.

Six adult rats were implanted with 100 ul pumps for 3 days, and then the pumps were replaced by similar ones with fresh solution as indicated in Example 2. Three animals had the pumps containing the inducer mix and three had saline as a control. At the end of the experiment the animals were anesthetized as indicated above and the penis (including the bulb), liver, and in some animals the cerebellum were surgically removed. The penile head and skin were excised and the organs were stored under liquid nitrogen.

NOS activity was determined from tissue homogenates from two treated and two control rats, not subjected to EFS in order to avoid the interference with residual L-NAME from the in vivo experiments and EFS-induced changes in NOS activity. Homogenates were prepared from each individual organ (approximately 300–400 mg), in 4 volumes of cold medium containing 0.32M sucrose/20 mM Hepes pH 7.2/0.5 mM EDTA/1 mM DTT, and protease inhibitors (3 uM leupeptin, 1 uM pepstatin A, 1 mM phenylmethyl sulfonylfluoride. The cytosol and particulate fractions were separated by centrifugation at 12,500 g for 60 min, and the particulate fraction was resuspended in an equal volume of medium. The cytosol fraction was passed through Dowex AG50WX-8 ($Na^+$) resin to remove endogenous arginine and 50 ul aliquots were incubated in triplicate for 45 min at 37 C as indicated previously, in the presence of 2 uCi/ml resin-purified (3-H) L-arginine, with or without L-NAME (2 mM), 0.3 mM aminiguanidine or EGTA (5 mM). After eliminating the residual (3-H)L-arginine through the resin, (3-H) citrulline was counted in the trichloroacetic acid ether-extracted supernatant. All values were corrected by the radioactivity eluted in time zero incubations.

FIG. 12 compares the NOS activity in the penile cytosol of untreated (control) rats, column labeled "C", with the iNOS inducer-treated rats, column labeled T. The 58% increase in NOS activity is clear. As FIG. 13 shows, this activity is 60–70% inhibited by L-NAME and not affected by aminoguanidine, AG. Since AG is a preferential inhibitor of macrophage iNOS as compared to nNOS, this evidence leads us to believe the iNOS induced in vivo is not the same as macrophage iNOS.

The effect of iNOS inducers in increasing penile NOS was confirmed by histochemical detection of NADPH diaphorase activity. One penis from a treated adult rat and one penis from a control adult rat were embedded in OCT compound frozen at −70° C., cut in 15 μm sections with a cryostat, and submitted to NAPDH diaphorase staining with tetrazolium blue. This activity is recognized as co-localizing with NOS in all tissues so far studied, including the rat penis. FIG. 14 shows the comparison of sections from untreated (top) and induced (bottom) rat penis. It is evident that while the dye is restricted to small faint areas in the untreated penis, it is very intense and widely distributed throughout the corpora cavernosa of the rat treated with iNOS inducers.

In summary, the preferred embodiment of our invention is based on the in vivo local continuous treatment of the rat penis with a mix of iNOS inducers to produce a considerable stimulation of the erectile response accompanied by an increase of penile NOS, which our evidence shows is the iNOS isozyme. The localized in vivo treatment surprisingly does not cause undesirable side effects that would be expected from systemic administration of iNOS inducers, and keeps the penile NOS actively under physiological control since no erection (priapism) is elicited in the absence of nerve stimulation. The demonstration and characterization of iNOS at the mRNA and protein levels in cells from the rat corpora cavernosa smooth muscle indicates that it plays a physiological role in the penis and allows for cloning its cDNA. Our evidence herein indicates it is a distinct species from other rat iNOS, including the vascular smooth muscle. Accordingly, our invention includes use of the corresponding recombinant iNOS cDNA, and those obtained from other species and penile cell types, are effective in increasing NOS synthesis in the penis under physiological control. Our invention provides an improved method for raising penile NOS levels to treat erectile dysfunction case.

It should be understood that various modifications within the scope of this invention can be made by one of ordinary skill in the art without departing from the spirit thereof. We therefore wish our invention to be defined by the scope of the appended claims as broadly as the prior art will permit, and in view of the specification if need be.

REFERENCES

1. Ignarro L. J., Bush P. A., Buga G. M., Wood K. S., Mukuto J. M., Rajfer J. Nitric oxide and cyclic GMP formation upon electric field stimulation cause relaxation of corpus cavernosum smooth muscle. *Biochem Biophys Reg. Comm.* 1990; 170:843–850.

2. Bush P. A., Aronson W. J., Buga G. M., Rajfer J. Ignarro L. J. Nitric oxide is a potent relaxant of human and rabbit corpus cavernosum. *J Urul* 1992; 147:1650–1655.

3. Rajfer J., Aronson W. J., Bush P., Dorey F. J., Ignarro L. J. Nitric oxide as a mediator of relaxation of the corpus cavernosum in response to nonadrenergic, noncholinergic neurotransmission. *N Engl J Med* 1992; 326: 90–94.

4. Lin M-C, Rajfer J. Swerdloff R. S., Gonzalez-Cadavid N. F. Testosterone down regulates the levels of androgen receptor mRNA in smooth muscle cells from the rat corpora cavernosa via aromatization to estrogens. *J Ster, Biochen & Mol Biol* 1993; 45:333–343.

5. Moriel E. Z., González-Cadavid N. F., Ignarro L. J., Hyrns R., Rajfer J. Serum levels of nitric oxide metabolites do not increase during penile erection. *Urology* 1993; 42:551–554.

6. Kaser M. Fuentes A., Swerdloff R. S., Rajfer J. Gonzalez-Cadavid N. F. Binding of penile nuclear proteins to the rat androgen receptor gene promoter correlates with androgen receptor gene expression. *Endocrine J* 1994; 2:589–586.

7. Burnett A. L., Lowenstein, C. J., Bredt D., Chang T. S. K., Snyder S. H. Nitric oxide: A physiologic mediator of penile erection. *Science* 1992; 25:401–403.

8. Burnett A. L., Tillman S. L., Change T. S. K., Epstein J. H., Lowenstein C. J., Bredt D. S., Snyder S. H., Walsh P. C. Immunohistochemical localization of nitric oxide synthase in the autonomic innervation of the human penis. *J. Urol* 1993; 150:73–76.

9. Dawson T. M., Bredt D. S., Fotuhi M., Hwang P. M., Snyder S. H. Nitric oxide synthase and neuronal NADPH diaphorase are identical in brain and peripheral tissue. *Proc Natl Acad Sci* 1991; 88:7797–7801.

10. Feldman H. A., Goldstein I, Hatzichriston D. G., Krane R. J., McKinlay J. B. Impotence and its medical and psychosocial correlates: results of the Massachusetts male aging study. *J Urol* 1994; 151:54–61.

11. Forstermann U., Schmidt H. H. H. W., Pollock J. S., Sheng H. Mitchell J. A., Warner T. D., Nakane M. Murad F. Isoforms of nitric oxide synthase. Characterization and purification from different cell types. *Biochem Pharmacol* 1991; 42:1849–1857.

12. Huang P. L., Dawson T. M., Bredt D. S., Snyder S. H., Wyman M. C. Targeted disruption of the neuronal nitric oxide synthase gene. *Cell* 1993; 75:1273–1286.

13. Katusic Z. S. Role of nitric oxide signal transduction pathway in regulation of vascular tone. *Intl Angiol* 1992; 11:13–19.

14. Lowenstein C. H. J., Dinerman J. L., Snyder S. H. Nitric oxide: A physiologic messenger. *Ann Int Med* 120:227–237.

15. Lue, T. (ed.) *World Book of Impotence*. Smith Gordon/Nishimura, London, 1992; pp. 264.

16. Moncada S., Higgs A. The L-arginine-nitric oxide pathway. *N Eng J Med* 1993, 329:2002–2012.

17. Nussler A. K., Billiard T. R. Inflammation, immunoregulation, and inducible nitric oxide synthase. *J Leukoc Biol* 1993; 54:171–178.

18. Saenz de Tejada I. In the physiology of erection, signposts to impotence. *Contemp Urol* 1992; ?:52–65.

19. Trigo-Rocha F., Hsu G. L., Donatucci C. F., Lue T. F. The role of cyclic adenosine monophosphate, cyclic guanosine monophosphate, endothelium nonadrengeic, nonchlolinergic neurotransmission in canine penile erection. *J Urol* 1993; 149:872–877.

We claim:

1. A method of treatment of erectile dysfunction in a patient comprising the steps of:
   a) providing an agent which produces an increase in in vivo penile tissue iNOS level;
   b) said agent is selected from at least one of the group consisting essentially of penile iNOS inducers, penile iNOS protein, penile iNOS cDNA, and penile iNOS cDNA-transformed penile cells or tissue;
   c) introducing an effective amount of said iNOS agent into penile tissue; and
   d) maintaining an effective level of said agent for a time period sufficient to produce NO in vivo in said penile tissue.

2. An erectile dysfunction treatment method as in claim 1 wherein:
   (a) said step of introduction includes introducing iNOS producing agent directly into in vivo penis tissue in an intermittent, continuous, or time-release basis.

3. An erectile dysfunction treatment method as in claim 2 wherein:
   a) said inducers are selected from the group consisting essentially of bacterial lipopolysaccharide, interferon-γ, tumor necrosis factor-α, interleukin-1β, and mixtures thereof.

4. An erectile dysfunction treatment method as in claim 1 wherein:
   (a) said agent is penile protein produced in vitro.

5. An erectile dysfunction treatment method as in claim 1 wherein:
   (a) said agent is penile iNOS cDNA.

6. An erectile dysfunction treatment method as in claim 1 wherein:
   (a) said agent is iNOS cDNA-transformed penile *Corpora cavernosa* cells.

7. Penile *Corpora cavernosa* iNOS.

8. Penile *Corpora cavernosa* iNOS cDNA.

9. Penile *Corpora cavernosa* cells genetically transformed with penile *Corpora cavernosa* iNOS cDNA.

10. An erectile dysfunction treatment method as in claim 5 wherein:
    a) said penile iNOS cDNA is administered locally to penile tissue by one or more of continuous infusion, single or repeated injection, topical application, intraurethral administration, and injection of microcapsules containing said penile iNOS cDNA.

11. An erectile dysfunction treatment method as in claim 6 wherein:
    a) said penile iNOS cDNA-transformed penile *Corpora cavernosa* cells as is administered locally to penile tissue by one or more of continuous infusion, single or repeated injection, topical application, intraurethral administration, and injection of microcapsules containing said penile iNOS cDNA.

* * * * *